US00PP30918P3

(12) United States Plant Patent
Klemm et al.

(10) Patent No.: US PP30,918 P3
(45) Date of Patent: Oct. 1, 2019

(54) ***DIANTHUS* PLANT NAMED 'KLEDG17296'**

(50) Latin Name: *Dianthus cullivars*
Varietal Denomination: KLEDG17296

(71) Applicant: Klemm+Sohn GmbH & Co. KG, Stuttgart (DE)

(72) Inventors: Nils Klemm, Stuttgart (DE); Lena Gutbrodt, Bempflingen (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 15/932,962

(22) Filed: May 30, 2018

(65) Prior Publication Data

US 2018/0352704 P1 Dec. 6, 2018

Related U.S. Application Data

(60) Provisional application No. 62/603,490, filed on May 31, 2017.

(51) Int. Cl.
*A01H 5/02* (2018.01)
*A01H 6/30* (2018.01)

(52) U.S. Cl.
USPC ..... Plt./276
CPC ..... *A01H 6/305* (2018.05)

(58) Field of Classification Search
USPC ..... Plt./276
See application file for complete search history.

(56) References Cited

PUBLICATIONS

UPOV hit on a *Dianthus* plant named 'KLEDG17296', filed Jul. 5, 2016, QZ PBR 2016/1677.*

* cited by examiner

*Primary Examiner* — Anne Marie Grunberg
(74) *Attorney, Agent, or Firm* — Barbara Campbell; Cochran Freund & Young LLC

(57) ABSTRACT

A new *Dianthus* plant designated 'KLEDG17296' particularly distinguished by light-pink semi-double flowers and an upright habit, is disclosed.

1 Drawing Sheet

Genus and species: *Dianthus* cultivars.
Variety denomination: 'KLEDG17296'.
A Community Plant Variety Rights application was filed for 'KLEDG17296' on Jul. 4, 2016, File No. 2016/1677.

BACKGROUND OF THE NEW PLANT 'KLEDG17296'

The present invention comprises a new and distinct variety of *Dianthus*, botanically known as *Dianthus* cultivars, and hereinafter referred to by the variety name 'KLEDG17296'. 'KLEDG17296' originated from a whole plant mutation from the *Dianthus* parent 'KLEDG12163' (U.S. Plant Pat. No. 24,707) in The Netherlands in 2015.

In August 2015, 'KLEDG17296' was first vegetatively propagated by vegetative stem cuttings. 'KLEDG17296' was found to reproduce true to type in successive generations of asexual propagation in Stuttgart, Germany via vegetative stem cuttings.

SUMMARY OF 'KLEDG17296'

The following are the most outstanding and distinguishing characteristics of 'KLEDG17296' when grown under normal horticultural practices in Stuttgart, Germany.

1. Light-pink semi-double flowers; and
2. An upright habit.

DESCRIPTION OF THE PHOTOGRAPH

This new *Dianthus* plant is illustrated by the accompanying photograph of a plant approximately 8-months old and grown in a greenhouse in Stuttgart, Germany. The photograph shows the whole plant, including the flowers and foliage and buds and were taken in May 2016 in Stuttgart, Germany. The colors shown are as true as can be reasonably obtained by conventional photographic procedures.

DESCRIPTION OF 'KLEDG17296'

The following detailed descriptions set forth the distinctive characteristics of 'KLEDG17296'. The data which define these characteristics were collected from asexual reproductions carried out in Stuttgart, Germany. Data was collected in April 2017 on 7-month old plants grown in a plastic greenhouse. Color references are to The R.H.S. Colour Chart of The Royal Horticultural Society of London (R.H.S.), 5$^{th}$ edition (2007).

Classification:
*Family.*—Caryophyllaceae.
*Botanical.*—*Dianthus* sp. or cultivars.
*Common.*—Pot carnation.
*Designation.*—'KLEDG17296'.

Parentage:
*Mutation parent.*—'KLEDG12163' (U.S. Plant Pat. No. 24,707).

Plant:
*Plant form.*—Upright, potted plant.
*Plant height.*—14.0 cm to 16.0 cm.
*Plant diameter or spread.*—16.0 cm to 18.0 cm.
*Propagation type.*—Vegetative stem cuttings.
*Time to produce a rooted young plant.*—14 to 16 days.
*Rooting habit* (*shape*).—Lanceolate.

Lateral branches:

*Length*.—Approximately 13.0 cm.

*Diameter*.—0.2 cm to 0.4 cm.

*Internode length*.—2.0 cm to 3.0 cm.

*Number of internodes per branch/stem*.—5 to 7.

*Node length*.—0.1 cm to 0.3 cm.

*Node diameter*.—0.2 cm to 0.3 cm.

*Texture*.—Smooth.

*Color*.—RHS 145B (Yellow-green).

*Branch/stem appearance*.—Solid.

Foliage:

*Arrangement*.—Opposite.

*Length*.—4.0 cm to 6.0 cm.

*Width*.—0.3 cm to 0.5 cm.

*Shape*.—Lanceolate.

*Apex*.—Acute.

*Base*.—Obtuse.

*Margin*.—Entire.

*Texture (both upper and lower surfaces)*.—Smooth.

*Immature leaf color*.—Upper surface: RHS 138A (Green). Lower surface: RHS 138A (Green).

*Mature leaf color*.—Upper surface: RHS N137A (Green). Lower surface: RHS N137A (Green).

*Venation pattern*.—Palmate.

*Venation color*.—Upper surface: RHS N137A (Green). Lower surface: RHS N137A (Green).

Flowers:

*Flower type and habit*.—Round, semi-double, numerous small sprays.

*Fragrance*.—Present.

*Natural flowering season*.—Spring to fall.

*Position of flowers relative to the foliage*.—Moderately above.

*Number of flowers per spray*.—4 to 6.

*Flower longevity on the plant*.—14 to 18 days.

*Buds*.—Length: 1.0 cm to 1.5 cm. Diameter: 0.4 cm to 0.6 cm. Shape: Elliptic. Color: RHS 138A (Green) and RHS 144A (Yellow-green). Extrusion of the styles at the bud stage: Absent.

*Corolla*.—Quantity of petals per flower: 8 to 10. Corolla height: 1.0 cm to 1.5 cm. Petal length: 2.0 cm to 2.5 cm. Petal width: 1.0 cm to 1.3 cm. Petal shape: Spoon-shaped. Petal apex: Obtuse. Petal base: Acute. Petal margin: Crenate. Depth of petal margin: Medium. Petal texture (both upper and lower surfaces): Smooth. Petal color: Immature: Upper surface: RHS N74C (Red-purple). Lower surface: RHS 76A (Purple). Mature: Upper surface: RHS 75B (Purple). Lower surface: RHS 76C (Purple).

*Calyx*.—Quantity of sepals per flower: Composed of 5 sepals. Shape: Campanulate. Calyx height: 0.8 cm to 1.2 cm. Calyx diameter (at the apex): 0.4 cm to 0.6 cm. Sepal texture (both upper and lower surfaces): Smooth. Sepal color: Upper surface: RHS 137A (Green). Lower surface: RHS 137D (Green).

Peduncles:

*Length*.—Approximately 13.0 cm from the soil to bud; 1.0 cm to 1.2 cm from the first nodium to the bud.

*Diameter*.—0.1 cm to 0.2 cm.

*Strength*.—Strong.

*Texture*.—Smooth.

*Color*.—RHS 137A (Green).

Reproductive organs:

*Stamens*.—Quantity per flower: Moderate. Filament length: 0.8 cm to 1.0 cm. Filament color: RHS 157B (Green-white). Anther length: 0.1 cm. Anther diameter: 0.05 cm. Anther color: RHS N155B (White). Pollen amount: Absent.

*Pistils*.—Not observed.

Fruit and seed set: Seed is sometimes observed, but no information on the seed is available.

Disease and pest/insect resistance: No disease and pest/insect resistance observed.

COMPARISON OF 'KLEDG17296' WITH PARENTAL LINE AND KNOWN VARIETY

'KLEDG17296' is distinguished from the mutation parent as described in Table 1.

TABLE 1

Comparison with Parental Line

| Characteristic | 'KLEDG17296' | Mutation Parent 'KLEDG12163' |
|---|---|---|
| Flower color | Light-pink | Pink with purple eyes |

'KLEDG17296' can be compared to the commercial *Dianthus* variety 'KLEDG12163' (U.S. Plant Pat. No. 24,707) and the commercial *Dianthus* variety 'KLEDG18305' (U.S. Plant patent application Ser. No. 15/998,600). Differences between the varieties are described in Table 2.

TABLE 2

Comparison with Similar Varieties

| Characteristic | 'KLEDG17296' | 'KLEDG12163' | 'KLEDG18305' |
|---|---|---|---|
| Flower color | Light-pink | Pink with purple eyes | Salmon pink with red ring |

We claim:

1. A new and distinct variety of *Dianthus* plant designated 'KLEDG17296' as illustrated and described herein.

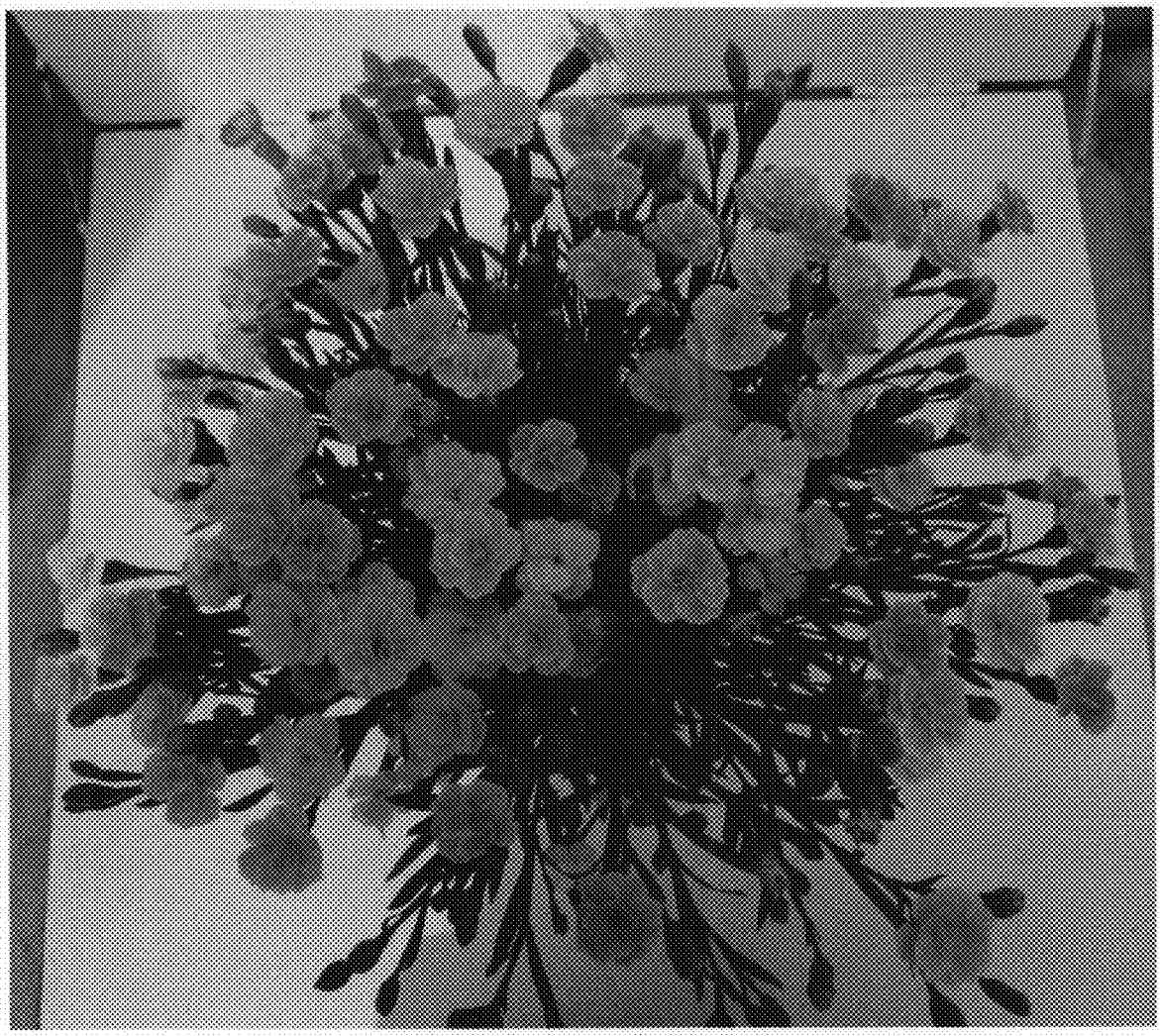

* * * * *